United States Patent [19]
Ehr et al.

[11] Patent Number: 6,033,433
[45] Date of Patent: Mar. 7, 2000

[54] STENT CONFIGURATIONS INCLUDING SPIRALS

[75] Inventors: Timothy G. J. Ehr, Elk River; Graig L. Kveen, Maple Grove, both of Minn.

[73] Assignee: Scimed Life Systems, Inc., Maple Grove, Minn.

[21] Appl. No.: 08/846,164

[22] Filed: Apr. 25, 1997

[51] Int. Cl.⁷ .................................................. A61F 2/06
[52] U.S. Cl. ................................................. 623/1; 623/12
[58] Field of Search .................................. 623/1, 11, 12; 606/191, 194–198, 108

[56] References Cited

U.S. PATENT DOCUMENTS

| | | | |
|---|---|---|---|
| 5,549,663 | 8/1996 | Cottone, Jr. ................................ | 623/1 |
| 5,759,174 | 6/1998 | Fischell et al. ........................... | 623/1 |
| 5,776,161 | 7/1998 | Globerman ................................ | 623/1 |
| 5,776,183 | 7/1998 | Kanesaka et al. ......................... | 623/1 |
| 5,827,321 | 10/1998 | Roubin et al. ............................ | 623/1 |
| 5,843,168 | 12/1998 | Dang ........................................ | 623/1 |
| 5,843,175 | 12/1998 | Frantzen .................................. | 623/1 |

FOREIGN PATENT DOCUMENTS

| | | |
|---|---|---|
| 0 722 700 A2 | 7/1996 | European Pat. Off. . |
| 297 02 671 U | 5/1997 | Germany . |
| 297 02 671 U1 | 5/1997 | Germany . |
| 297 08 879 U | 9/1997 | Germany . |
| 96/03092 | 2/1996 | WIPO . |
| 96/26689 | 9/1996 | WIPO . |
| 97/32543 | 9/1997 | WIPO . |
| 97/32544 | 9/1997 | WIPO . |
| 97/33534 | 9/1997 | WIPO . |

*Primary Examiner*—Mickey Yu
*Assistant Examiner*—Tram A. Nguyen
*Attorney, Agent, or Firm*—Vidas, Arrett & Steinkraus

[57] ABSTRACT

The invention is directed to an expandable stent which is longitudinally flexible in both the unexpanded and expanded conditions. The stent includes spiral structures which at least partially unwind upon expansion of the stent to limit stent recoil. Regions of low strain in the stent during expansion are provided by the spiral structures.

13 Claims, 11 Drawing Sheets

STENT CONFIGURATIONS INCLUDING SPIRALS

BACKGROUND OF THE INVENTION

1. Field of the Invention

This invention relates to stents of improved configuration which incorporate spiral articulations which unwind to form bracing structures or scaffolding upon expansion.

2. Brief Description of the Prior Art

Stents are radially expandable endoprosthesis which are typically intravascular implants capable of being implanted transluminally and enlarged radially after being introduced percutaneously. They have also been implanted in urinary tracts and bile ducts. They are used to reinforce body vessels and to prevent restenosis following angioplasty in the vascular system. They may be self-expanding or expanded by an internal radial force, such as when mounted on a balloon.

In the past, stents have assumed many configurations and been made of many materials, including metals and plastic. Ordinary metals such as stainless steel have been used as have shape memory metals such as nitinol and the like. Stents have also been made of biodegradable plastic materials. They have been formed from wire, tube stock, etc.

SUMMARY OF THE INVENTION

This invention provides a new configuration for stents which may be adapted by all of the various types of prior art stents referred to hereinabove. There are numerous advantages to the new configuration. It limits recoil and adds resistance to compression for the expanded stent, among other things. It is longitudinally flexible in both the unexpanded and expanded conditions. It has several embodiments.

An important part of the new configuration includes a spiral or spiral-like structure comprised of joined elements which are coiled or bent and which unwind, uncoil or unbend to a more or less straightened condition on expansion of the stent. Such structures are hereinafter referred to collectively as spiral, spirals or spiral-like structures. These structures provide regions of low strain in the stent during expansion. These elements may be joined to each other or to any radially expansive members of any kind, annular serpentine members being preferred.

DETAILED DESCRIPTION OF THE PREFERRED EMBODIMENTS

Figure 1:
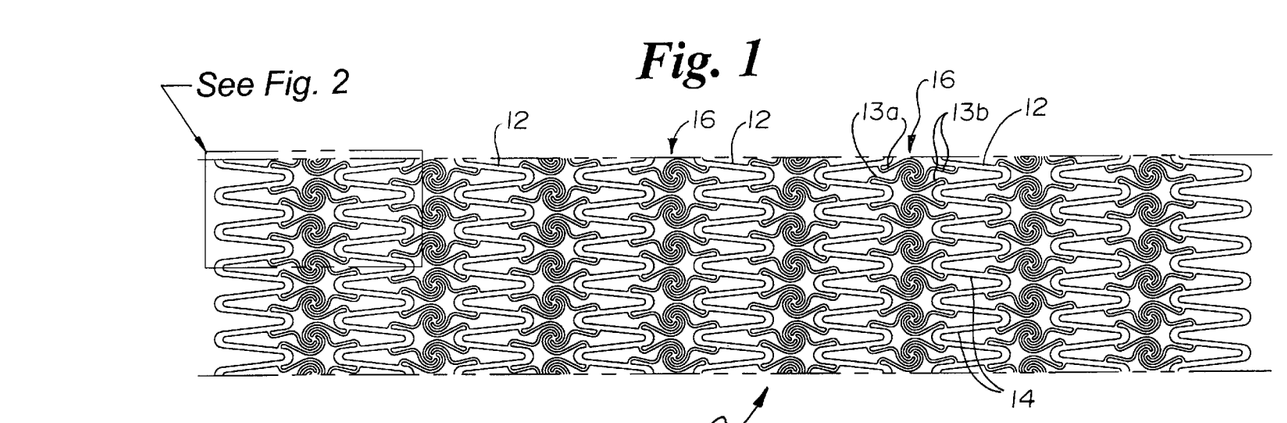
FIG. 1 is a flat view of one pattern embodiment of a stent configuration of the invention (unexpanded)
Figure 2:
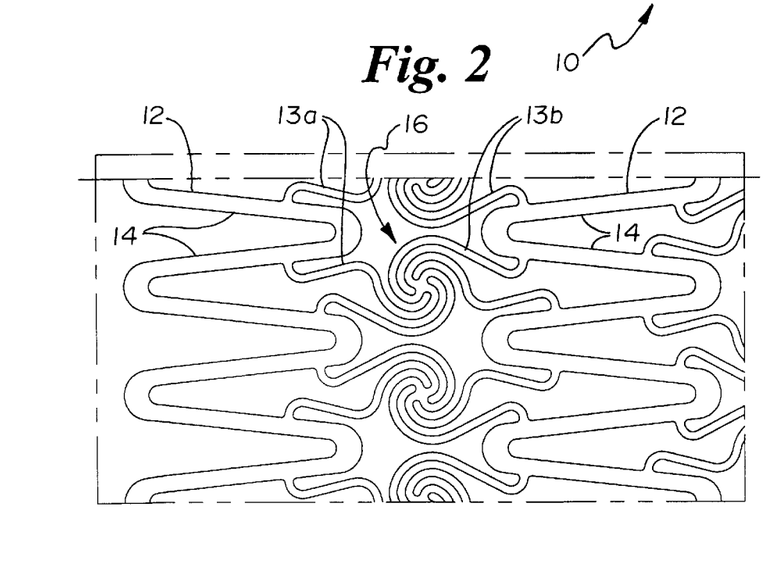
FIG. 2 is a detail of a portion of FIG. 1.
Figures 3, 4:
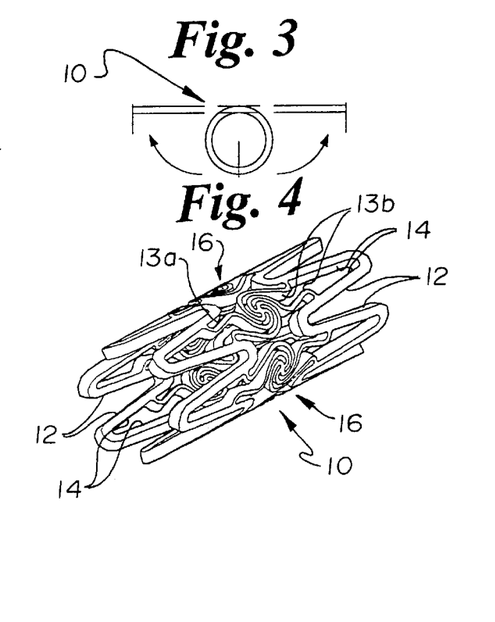
FIG. 3 is an end view of a stent of the FIG. 1 pattern according to the invention showing it in tubular configuration.
FIG. 4 is a showing of a stent in the embodiment of the preceding Figures in perspective and in an unexpanded configuration.
Figure 6:
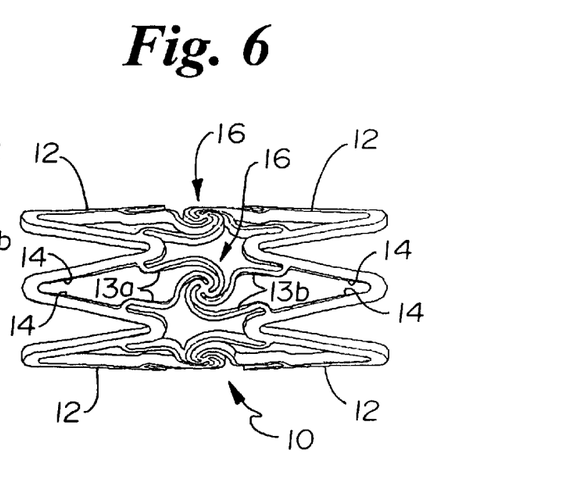
FIGS. 6, 7 and 8 are showings of the stent of FIG. 4 in various stages of expansion with only details of the front of the stent shown for simplicity.
Figure 7:
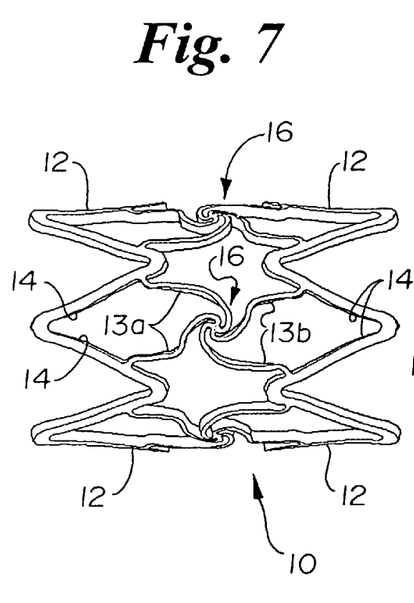
Figure 8:
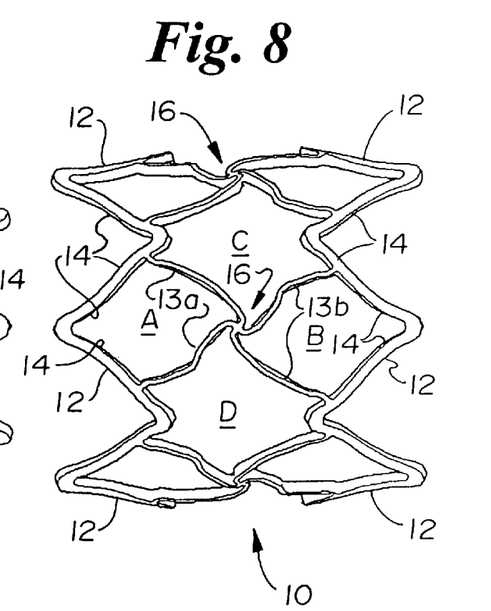

One preferred embodiment of the invention is illustrated in FIGS. 1–8. It comprises a metal tube-like structure 10 as best shown in FIGS. 3 and 4, such as nitinol or stainless steel, which has been etched or laser cut to the configuration shown in the plan view of FIGS. 1 and 2 and in a short version as shown in FIG. 4. The configuration is made up of a series of serpentine annular expandable elements or segments 12 which form loops 14 to allow for radial annular expansion. Segments 12 may be other configurations but serpentine is preferred. Elements 12 are interconnected by pairs of elongated members 13a and 13b which are attached at one end to successive loops 14 of a segment 12 and which are joined at their other ends to adjacent pairs of elongated members 13a and 13b, as best seen in detail in FIG. 2. Members 13a and 13b are preferably of narrower gauge than members 12 and are joined together in a coiled or spiral arrangement as shown generally at 16. Spiral 16 forms a structure about which members 13 may uncoil or unwind in a counterclockwise direction or clockwise direction to a substantially straight condition, depending on the spiral winding direction, upon radial expansion of members 12. In this embodiment spirals 16 are formed in alternate wound structures so that some unwind in one direction and some in the other direction. Of course, in any embodiment the spirals can be formed so that they all unwind in one direction, either clockwise or counterclockwise and they may have more or fewer members 13. Also, more or less spirals may be included between the segments. The unwinding is accompanied by a straightening action with respect to members 13 as is described in more detail in connection with FIGS. 4–8. It can be seen from FIGS. 4 through 8 that the resultant configuration in an expanded stent of this configuration is comprised of a plurality of cells, the perimeter of each of which is defined by a pair of members or struts defined by the loop portion 14 of segment 12 and a pair of members or struts 13. The cells are joined at 16 as best seen in FIG. 8. More specifically the cells are of two kinds as shown in FIG. 8. A first pair of cells are A and B made up of a segment 12 and two struts 13a for cell A or 13b for cell B. A second pair of cells are C and D made up of an inward loop portion 14 of segment 12 and a strut 13a and a strut 13b for cells C and D.

Figure 5:
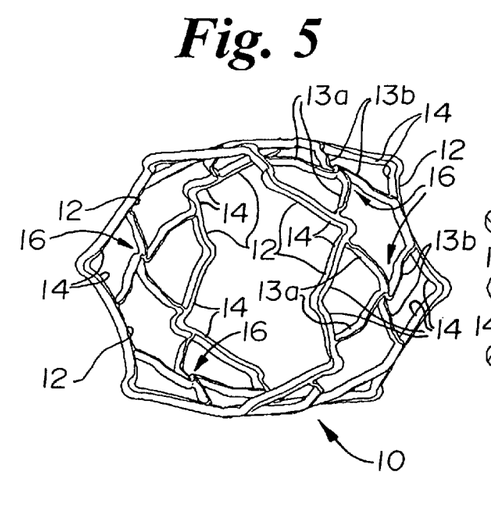
FIG. 5 is a showing of the stent of FIG. 4 fully expanded with details of the front and rear of the stent.

When a stent of the invention, such as that shown in FIGS. 1–4 undergoes expansion, such as from the embodiment of FIG. 4, it will appear as shown in FIG. 5 in the fully expanded condition. FIG. 5 shows the stent in perspective.

The unwinding action which the spiral elements 16 undergo upon stent expansion is best seen in FIGS. 6–8 which show only the front side surface of the stent for simplicity and clarity.

As radial expansion begins (seen in FIG. 6) it can be appreciated that the spiral elements 16 undergo an unwinding or straightening action by a pulling force on all of the members 13. Specifically, as expansion occurs, elements 13 undergo a straightening action as can be seen in the early stages of expansion in FIG. 6.

Upon further expansion (seen in FIG. 7), spirals 16 undergo further unwinding, i.e., elements 13 undergo further straightening.

Finally in FIG. 8, substantial full expansion provides substantially straightened elements 13 which in that condition limit stent recoil and increase the resistance to compression of the stent.

Figure 9:
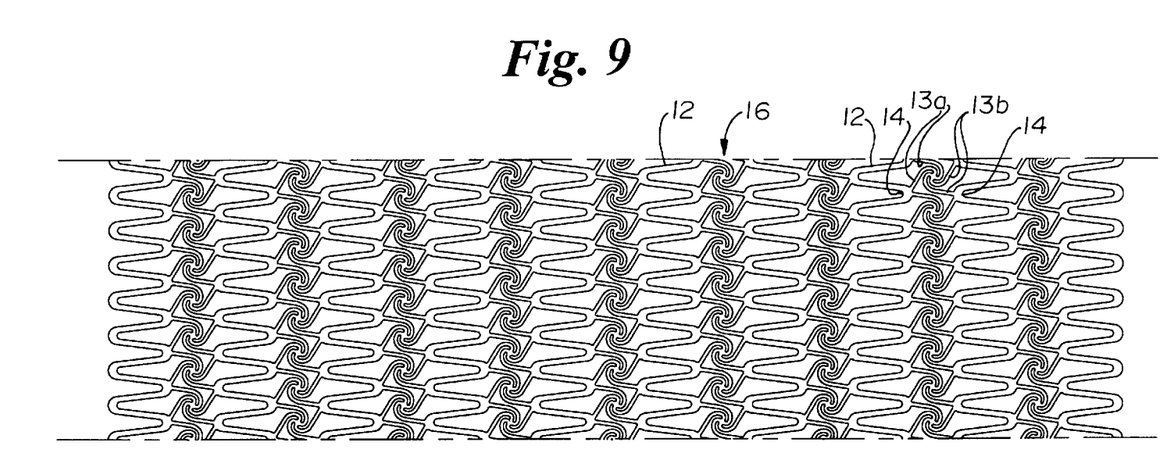
FIG. 9 is a plan view showing another embodiment of the invention.

FIG. 9 shows a modified embodiment in which elements 13a and 13b contact segment 12 at the end of its loops 14. Also note in this embodiment that the spirals 16 are all wound in the same direction.

Figure 10:
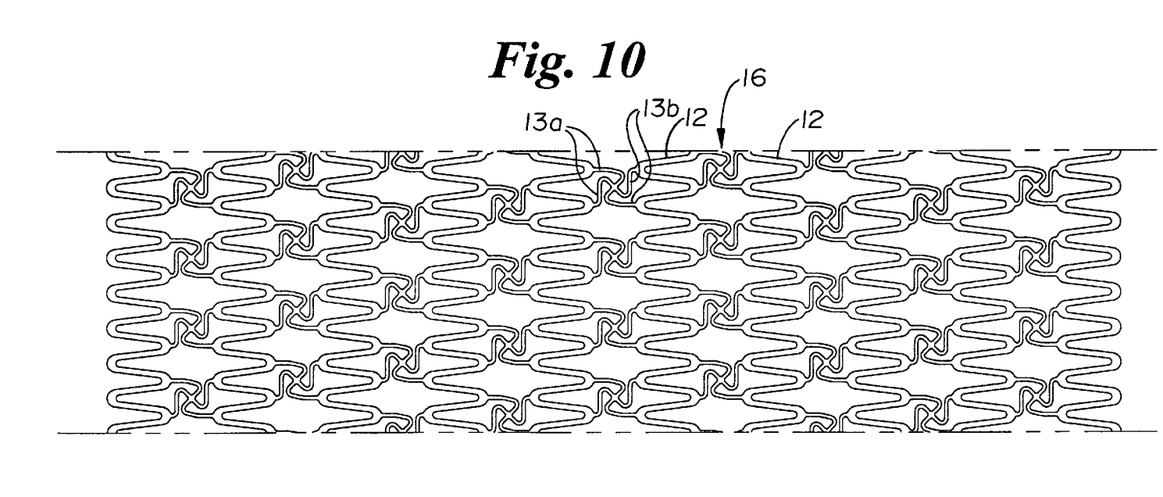
FIG. 10 is a showing of a modified embodiment.

FIG. 10 shows an embodiment of the invention in which the spiral members 13 are more bent and less curvilinear but still form a spiral-like configuration 16. The remainder of the configuration is similar to that of FIG. 9. In FIG. 10, elongate members 13 are shown prior to expansion of the stent. When the stent is expanded, members 13 unwind counter-clockwise and straighten somewhat. At full expansion members 13 straighten still further and straighten substantially so as to provide resistance to compression of the stent and low recoil. The expanded configuration displays a cell configuration similar to that seen in FIG. 8.

Figure 11:
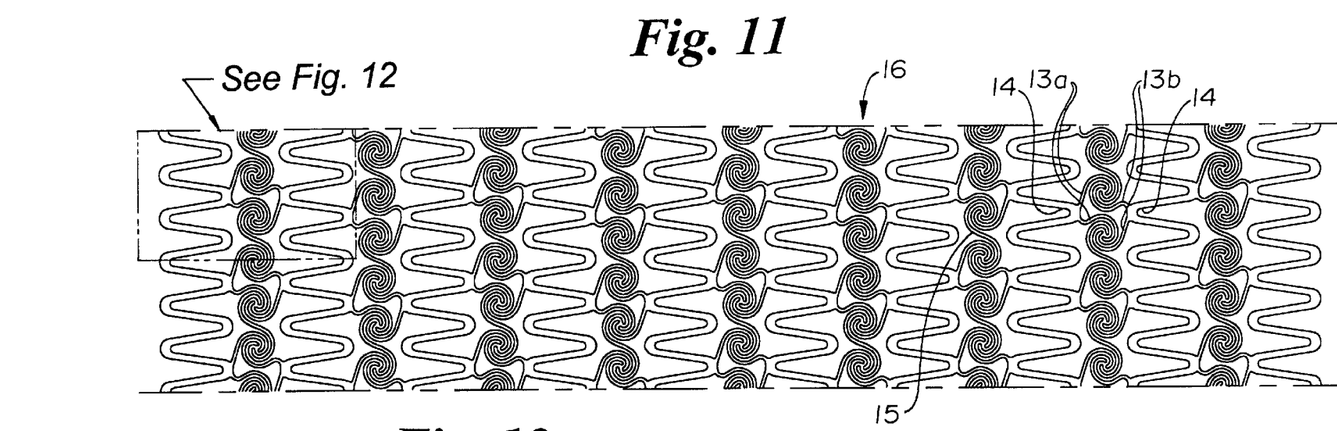
FIG. 11 is a showing of another embodiment.
Figure 12:
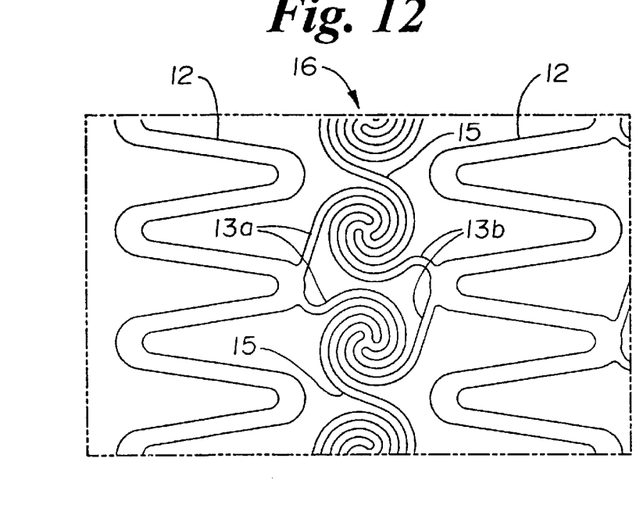
FIG. 12 is a detail of a portion of FIG. 11.
Figure 13:
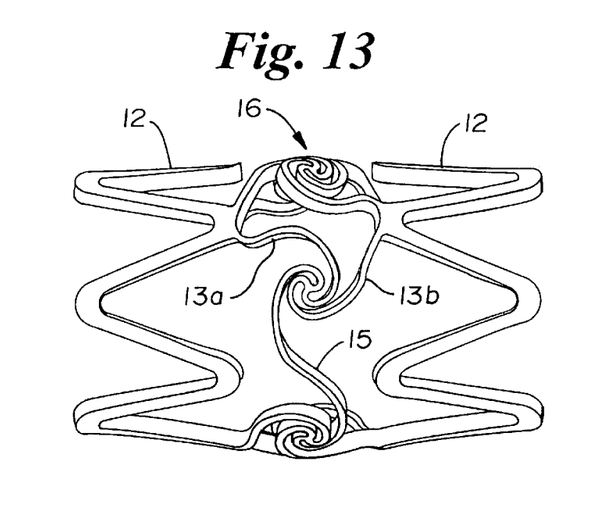
FIG. 13 is a showing of the stent of FIGS. 11 and 12 in an expanded configuration.

Other embodiments are shown in subsequent Figures with different spiral arrangements. For example, the embodiment of FIGS. 11–13 shows spiral arrangements 16 which are wound in the same direction and elements 13 attached at the end of loops 14 while some adjacent spirals between segments are interconnected by members 15.

Figure 14:
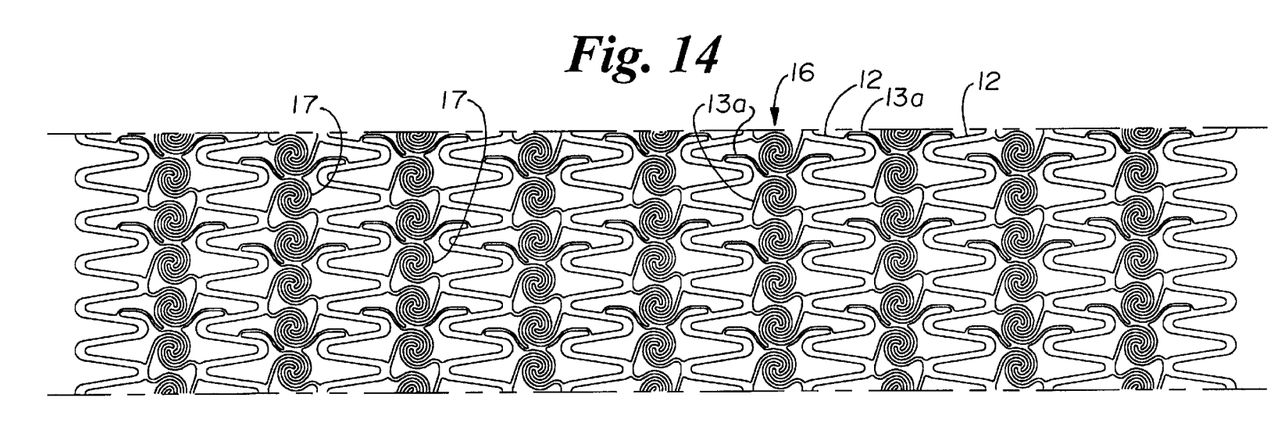
FIG. 14 is a showing of another embodiment.

FIG. 14 shows some elements 13 in a spiral 16 contacting the end of loops 14 and some contacting segment 12 proper. Also, some adjacent spirals are interconnected by members 17.

Figure 15:
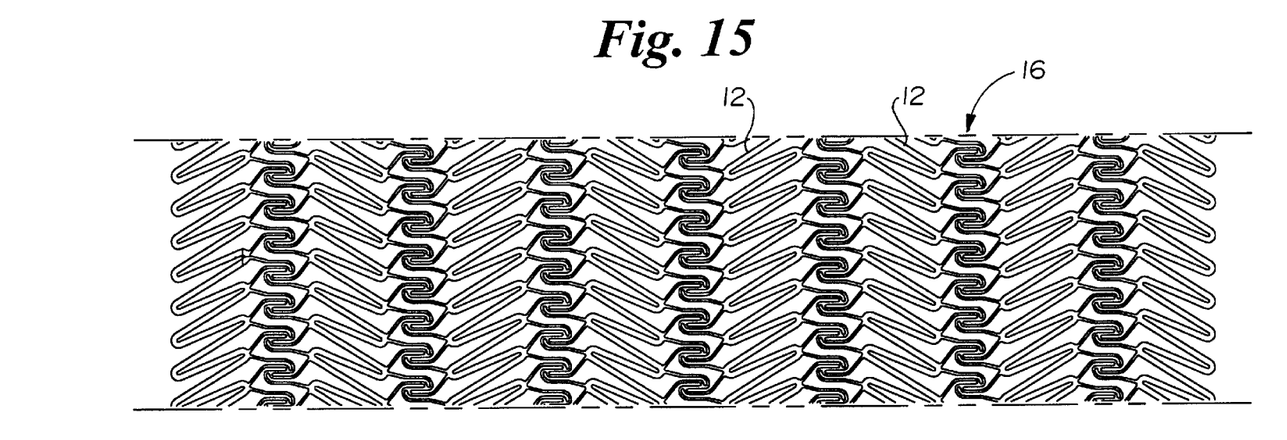
FIG. 15 is a showing of still another embodiment.

FIG. 15 shows a flattened or elongated spiral arrangement 16 and elements 12 are angled with respect to the longitudinal axis of the stent. In previous embodiments, these elements or segments have been arranged parallel to the axis or horizontal. Elongated spirals as in FIG. 13 and spirals of previous Figures may be mixed together. (Not shown).

Figure 16:
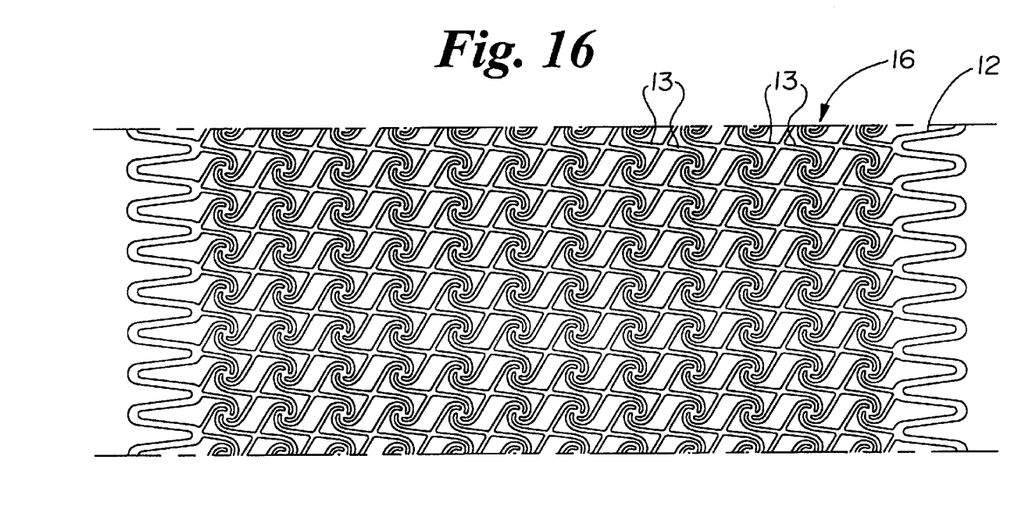
FIG. 16 is a showing of yet another embodiment.

In the embodiments already discussed, annular expandable segments such as segments 12 are interspersed with spiral arrangements 16. However, as can be seen in FIG. 16, at least a substantial portion or all of the stent body can be merely comprised of spiral arrangements 16 connected to each other. Actually, all of the body may consist of spirals. In this embodiment, the elements 13 interconnect between spirals over substantially the entire body of the stent. Optionally, the ends may include segments 12 as shown.

Figure 17:
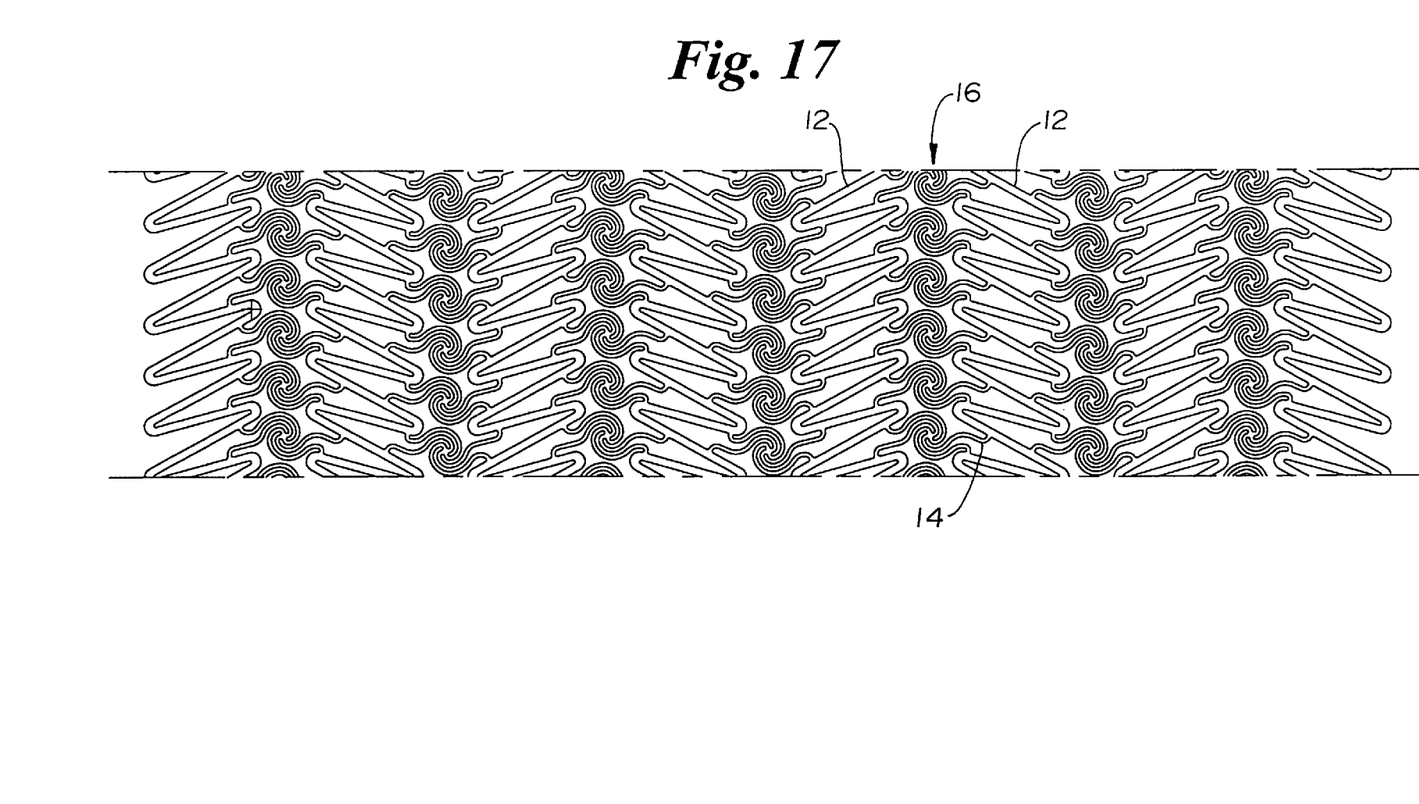
FIG. 17 is a showing of still another embodiment.
Figure 18:
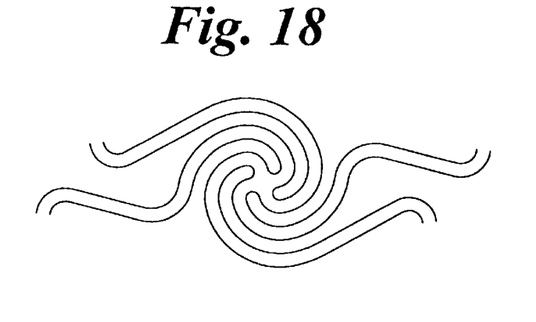
FIGS. 18–28 show various spiral-like arrangements of the invention.
Figure 19:
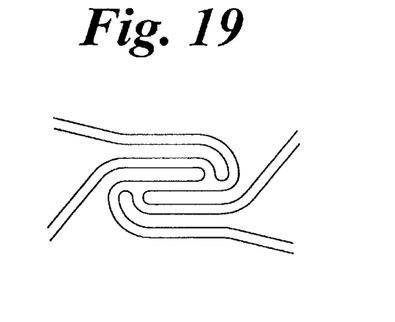
Figure 20:
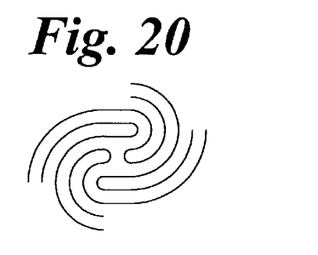
Figure 21:
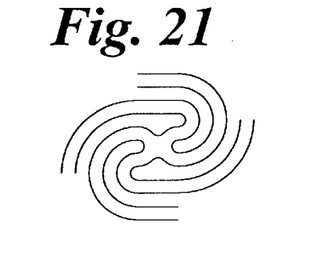
Figure 22:
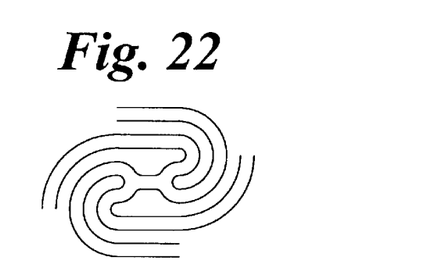
Figure 23:
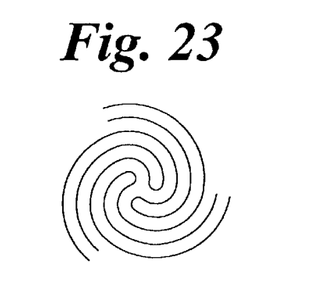
Figure 24:
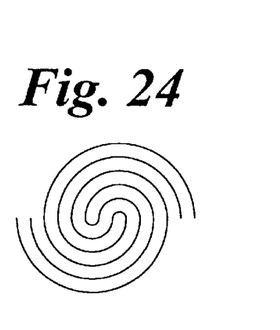
Figure 25:
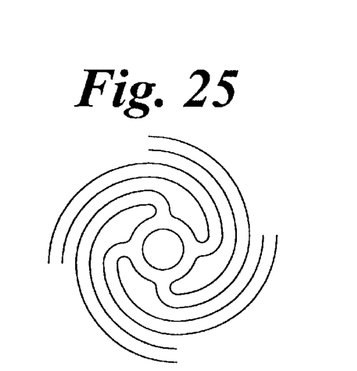
Figure 26:
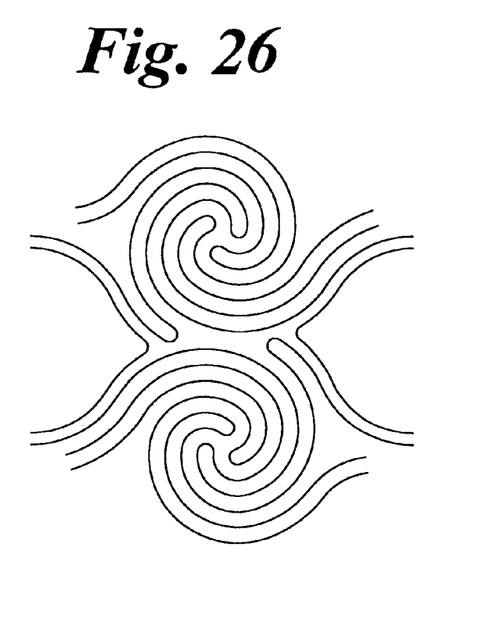
Figure 27:
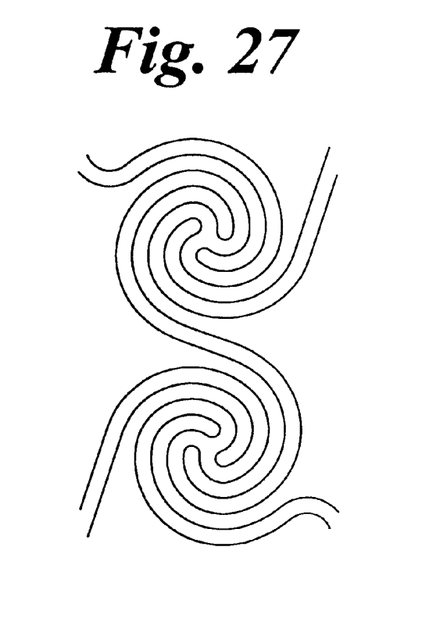
Figure 28:
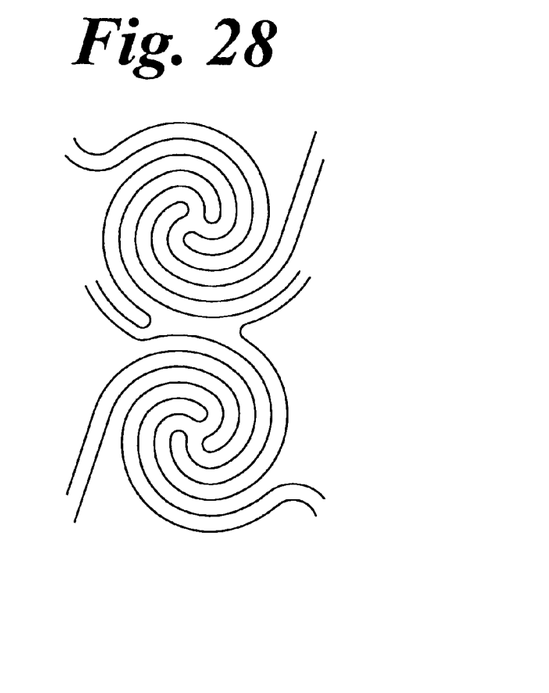

The embodiment shown in FIG. 17 shows segments 12 alternately angled in opposite directions and with legs thereof of different length and elements 13 contacting the segments at different locations, i.e., as at the loop portion 14 and at the segment portion proper.

FIGS. 18–28 demonstrate examples of what is meant by the terms, spiral and spiral-like herein. Of course, additional members may be included in the spirals.

Figure 29:
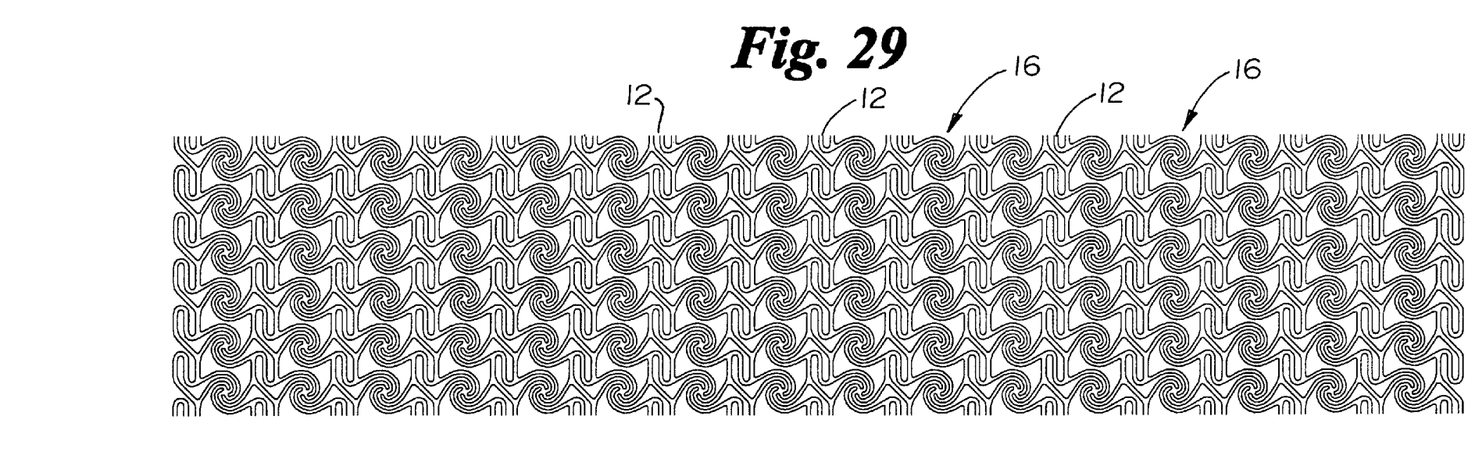
FIG. 29 shows another embodiment of the invention.

FIG. 29 shows segments 12 in a configuration other than the annular serpentine configuration of previous Figures.

Figure 30:
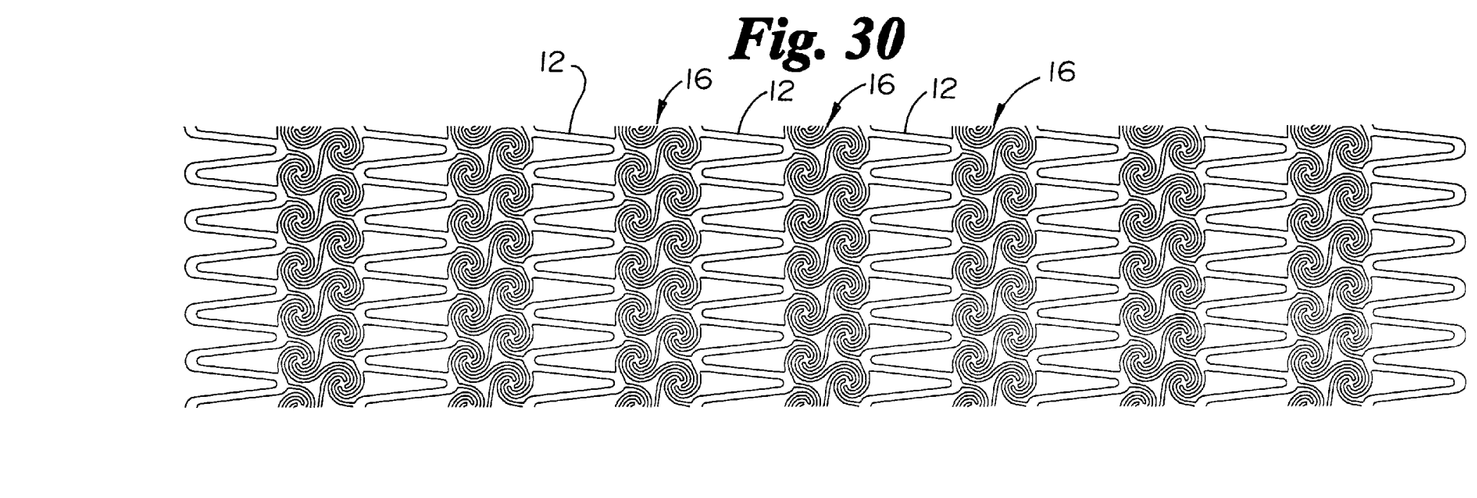
FIG. 30 shows yet another embodiment.

FIG. 30 shows alternate segments 12 in serpentine annular configuration interconnected by double rows of interconnected coil configurations 16.

Figure 31:
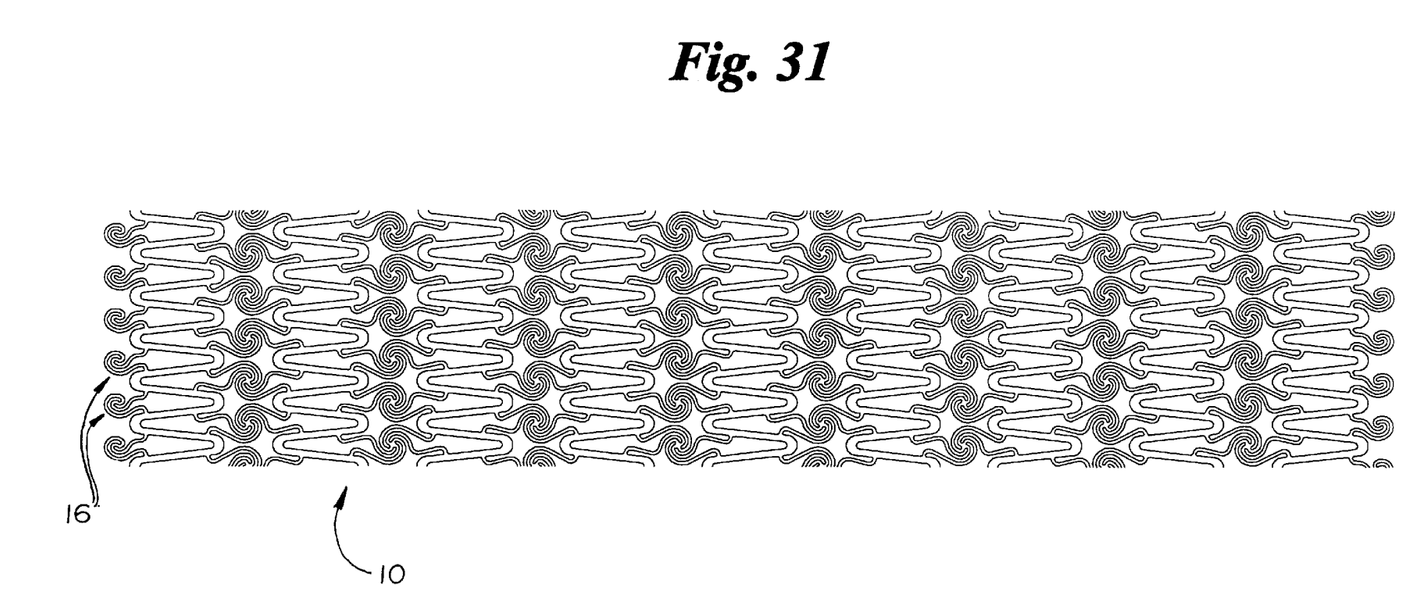
FIG. 31 shows still another embodiment of the invention.

FIG. 31 is included to demonstrate that spirals 16 may be included on the ends of a stent 10.

While this invention may be embodied in many different forms, there are described in detail herein specific preferred embodiments of the invention. This description is an exemplification of the principles of the invention and is not intended to limit the invention to the particular embodiments illustrated.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. An expandable stent in the form of a generally tubular body formed of interconnected spiral elements, each spiral element formed of a plurality of spiral members, at least one spiral member of each spiral element intersecting at least one spiral member of a circumferentially adjacent spiral element in an oblique angle.

2. The stent of claim 1 including annular serpentine elements at the ends of the stent.

3. A stent comprised of:
   a plurality of longitudinally aligned and expandable segments of generally cylindrical configuration;
   a pair of connector elements extending from a segment to join a corresponding pair of connector elements extending from an adjacent segment, the connector elements forming a spiral configuration between the segments, the connector elements at least partially unwinding upon expansion of the adjoining segments.

4. The stent of claim 3 wherein at least two of the connecting elements extend in a substantially longitudinal direction.

5. The stent of claim 3 wherein the connecting elements are substantially curvilinear.

6. A stent comprised of:
   a plurality of expandable segments of annular serpentine configuration, each segment having a plurality of loops, the loops having ends;
   connector elements extending between adjacent serpentine segments, the connector elements forming spiral configurations between the segments, the spiral configurations formed exclusively of connector elements terminating in annular segments, each spiral configuration defined by a center about which the connector elements spiral, all of the connector elements spiraling in excess of a quarter revolution about the center.

7. The stent of claim 6 wherein the connector elements extend from the loop ends.

8. The stent of claim 6 wherein the spiral configurations are arranged in rows, the rows of spirals alternating with the expandable segments along the stent.

9. The stent of claim 6 wherein the loops are oriented at an oblique angle relative to the longitudinal axis of the stent.

10. The stent of claim 6 wherein each loop includes a portion which is oriented in a substantially circumferential direction.

11. A stent comprised of:
   a plurality of expandable segments of annular serpentine configuration, each segment having a plurality of loops, the loops having ends;

connector elements extending between adjacent serpentine segments, the connector elements forming spiral configurations between the segments, the spiral configurations formed exclusively of connector elements terminating in annular segments, the spiral configurations arranged in rows, the rows of spirals alternating with the expandable segments along the stent, wherein pairs of adjacent spiral configurations extend from a common loop end.

12. An expandable stent in the form of a generally tubular body formed of interconnected spiral elements, each spiral element comprising a plurality of connector elements which are spiraled about a center, each connector element spiraled in excess of a quarter revolution about the center, each spiral element formed of at least three connector elements.

13. An expandable stent in the form of a generally tubular body formed of interconnected spiral elements, each spiral element comprising a plurality of connector elements which are spiraled about a center, each connector element spiraled in excess of a quarter revolution about the center, the stent further comprising expandable segments of annular serpentine configuration forming a plurality of loops having ends, each spiral element having at least two connector elements connected to adjacent expandable segments.

* * * * *